United States Patent [19]

Tan et al.

[11] Patent Number: 5,157,132
[45] Date of Patent: Oct. 20, 1992

[54] INTEGRATED PROCESS FOR RECOVERY OF CAROTENOIDS AND TOCOTRIENOLS FROM OIL

[75] Inventors: Barrie Tan; Mohammed H. Saleh, both of Amherst, Mass.

[73] Assignee: Carotech Associates, Amherst, Mass.

[21] Appl. No.: 525,545

[22] Filed: May 18, 1990

[51] Int. Cl.⁵ .............................. C07D 311/74
[52] U.S. Cl. .................... 549/413; 585/351; 549/335; 549/410; 554/157; 554/167; 554/175; 554/193; 554/209
[58] Field of Search .............. 549/413, 410, 338; 260/398, 413, 410.9 R; 585/351

[56] References Cited

U.S. PATENT DOCUMENTS

| Re. 22,629 | 4/1945 | Barnett | 585/803 |
| 2,032,006 | 2/1936 | Cross | 585/803 |
| 2,032,165 | 2/1936 | Barnett | 99/22 |
| 2,318,747 | 5/1943 | Buxton | 585/803 |
| 2,327,766 | 8/1943 | Cawley | 260/428.5 |
| 2,345,097 | 3/1944 | Buxton | 260/428.5 |
| 2,432,021 | 12/1947 | Larner | 260/428.5 |
| 2,484,040 | 10/1949 | Lange et al. | 260/666 |
| 2,527,602 | 10/1950 | Wall | 585/803 |
| 2,652,433 | 9/1953 | Blaizot | 260/664 |
| 2,741,644 | 4/1956 | Blaizot | 260/666 |
| 4,438,629 | 3/1984 | Ruegg | 585/803 |

FOREIGN PATENT DOCUMENTS

| 59-005178A | 12/1984 | Japan. |
| 63-005074A | 1/1988 | Japan. |
| 61109764A | 5/1988 | Japan. |
| 63-132871A | 6/1988 | Japan. |
| 63-005073A | 11/1988 | Japan. |
| 63-295551A | 12/1988 | Japan. |
| 1562794 | 3/1980 | United Kingdom. |
| 2160874A | 1/1986 | United Kingdom. |
| 2212806A | 8/1989 | United Kingdom. |
| 2218989A | 11/1989 | United Kingdom. |

OTHER PUBLICATIONS

Tan, et al., *Analy. Biochem.*, 180: 368-373 (1989).

Primary Examiner—Michael L. Shippen
Assistant Examiner—Deborah D. Carr
Attorney, Agent, or Firm—Hamilton, Brook, Smith & Reynolds

[57] ABSTRACT

A process and apparatus is disclosed for separation of fatty acid alkyl esters, carotenoids and tocotrienols from oil. Fatty acids in a vegetable oil are subjected to alcoholic esterification to form an ester-rich layer including fatty acid alkyl esters, carotenoids and tocotrienols. The ester-rich layer is exposed to solvolytic micellization to form a carotenoid-rich layer. The ester-rich layer is separated from the carotenoid-rich layer. The carotenoids in the carotenoid-rich layer are concentrated and can be adsorptively separated from the carotenoid-rich layer. Fatty acid alkyl esters are separated from the ester-rich layer to form a tocotrienol-rich layer. Individual tocotrienols in the tocotrienol-rich layer are adsorptively separated and concentrated.

22 Claims, 1 Drawing Sheet

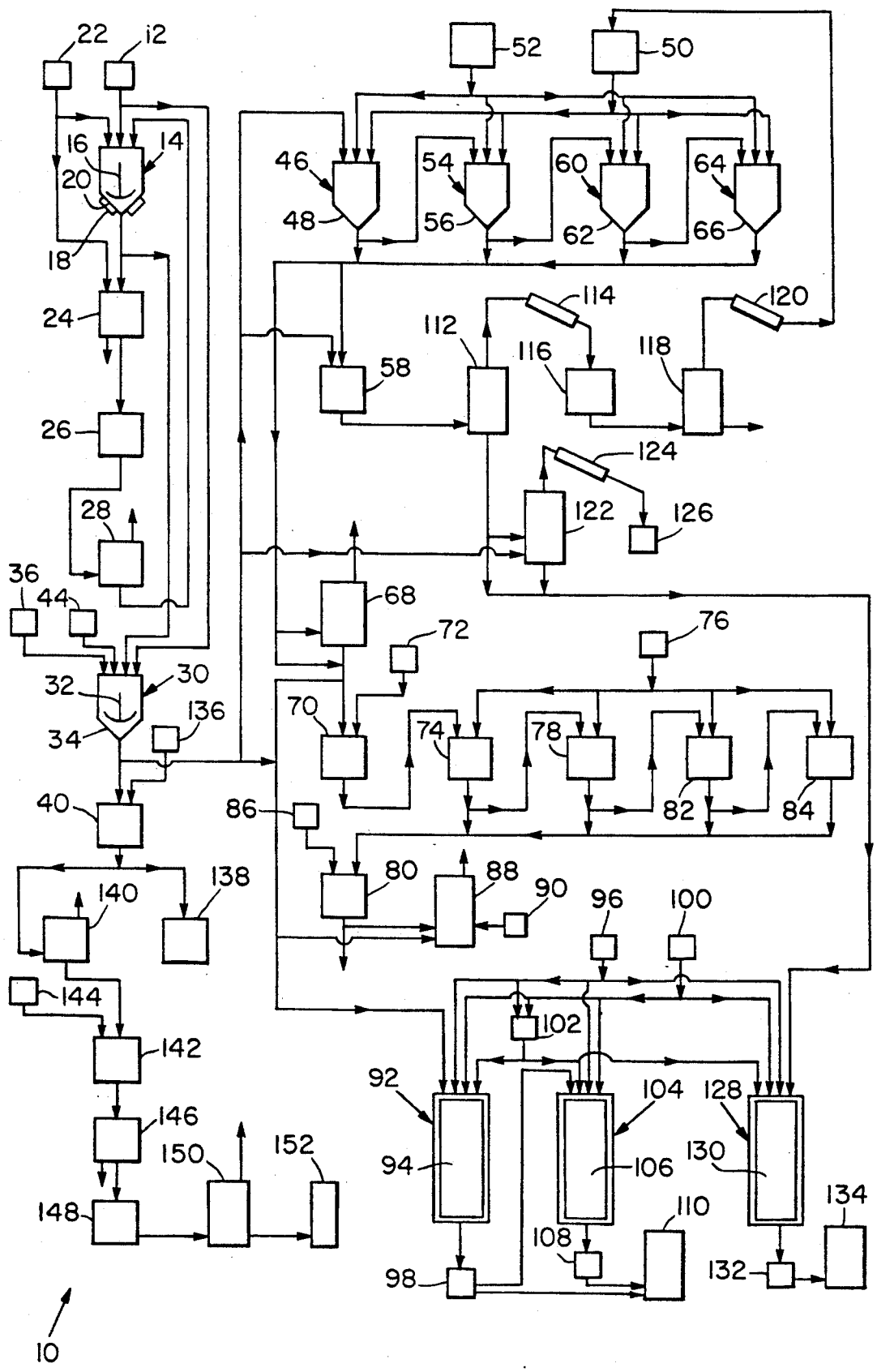

INTEGRATED PROCESS FOR RECOVERY OF CAROTENOIDS AND TOCOTRIENOLS FROM OIL

BACKGROUND OF THE INVENTION

Carotenoids and tocotrienols found in oils of plant origin have many applications.

Carotenoids are typically used for pigmentation of foods and medicine. They have also been found to inhibit light-initiated flavor deterioration of soybean oil without affecting color quality. Warner et al., *J. Am. Oil Chem. Soc.*, 64:213 (1987). β-carotene is a precursor to vitamin A and, in addition to being a dietary vitamin supplement, has been associated with prevention of epithelial and endothelial cell cancer. Nutrition Policy Board, *Summary and Recommendation of the Surgeon General's Report on Nutrition and Health*, U.S. Dept. of Health and Human Services, publication 88-50211 (1988); Menkes et al., *New Eng J. Med.*, 20: 1250 (1986).

Tocotrienols have been implicated in suppression of cholesterolgenesis and of arterial thrombosis by inhibition of platelet thromboxane formation. Qureshi et al., *Amer. Chem. Soc. Nat'l. Mtg.* (April, 1990); Rand et al., *Lipids*, 23:1019 (1988). Tocotrienols have also been investigated as possible anticarcinogenic agents. Komiyama et al., *Int'l. Palm Oil Dev. Conf.*, PORIM Press, Kuala Lumpur, Malaysia (1988); Ngah et al., *Int'l. Palm Oil Dev. Conf.*, PORIM Press, Kuala Lumpur, Malaysia (1988).

Historically, separation of carotenoids and tocotrienols has been incomplete. For example, carotenoids have been extracted from crude palm oil but tocotrienols typically are lost during the extraction process. Likewise, carotenoids are generally lost during extraction of tocotrienols from oils. Also, know methods for recovering carotenoids and tocotrienols typically do not provide for individual separation of classes of carotenoids and tocotrienols.

Therefore, a need exists for a new method and apparatus for extracting carotenoids and tocotrienols from oil which overcome or minimize the above-listed problems.

SUMMARY OF THE INVENTION

The present invention relates to a process and apparatus for extracting carotenoids and tocotrienols from oils.

A process for extracting carotenoids and tocotrienols from oils includes contacting the oil with a lower alkyl alcohol in the presence of a base under conditions sufficient to convert glycerides in the oil to fatty acid alkyl esters and glycerol and to form an ester-rich layer and a glycerol-rich layer. The ester-rich layer is then separated from the glycerol-rich layer. The ester-rich layer is contacted with a lower alkyl alcohol and water under conditions sufficient to cause solvolytic micellization of the ester-rich layer without destroying the carotenoids and tocotrienols, thereby forming a carotenoid-rich layer. The ester-rich layer is separated from the carotenoid-rich layer. The lower alkyl alcohol is separated from the ester-rich layer under conditions sufficient to prevent destroying the tocotrienols in the ester-rich layer. Fatty acid alkyl esters are separated from the ester-rich layer under conditions sufficient to prevent destroying the tocotrienols, thereby forming a tocotrienol-rich layer. Individual tocotrienols in the tocotrienol-rich layer are then adsorptively separated and concentrated.

Apparatus for extracting carotenoids and tocotrienols from oils includes means for contacting the oil with a lower alkyl alcohol in the presence of a base under conditions sufficient to convert glycerides in the oil to fatty acid alkyl esters and glycerol and to form an ester-rich layer and a glycerol-rich layer. Means for separating the ester-rich layer from the glycerol-rich layer separate the ester-rich layer form the glycerol-rich layer. Means for contacting the ester-rich layer with a lower alkyl alcohol and water contact the ester-rich layer with a lower alkyl alcohol and water under conditions sufficient to cause solvolytic micellization of the ester-rich layer without destroying the carotenoids and tocotrienols, thereby forming a carotenoid-rich layer. Means for separating the ester-rich layer from the carotenoid-rich layer separate the ester-rich layer from the carotenoid-rich layer. Means for separating the lower alkyl alcohol from the ester-rich layer separate the lower alkyl alcohol from the ester-rich layer under conditions sufficient to prevent destroying the tocotrienols in the ester-rich layer. Means for separating the fatty acid alkyl esters from the ester-rich layer separate fatty acid alkyl esters from the ester-rich layer under conditions sufficient to prevent destroying the tocotrienols, thereby forming a tocotrienol-rich layer. Means for adsorptively separating and concentrating individual tocotrienols adsorptively separate and concentrate individual tocotrienols in the tocotrienol-rich layer.

This invention has many advantages. In general, an integrated process is provided which separates both carotenoids and tocotrienols from oils. Further, individual classes of tocotrienols and carotenoids can be separated and recovered. Other components of tocotrienol- and carotenoid-containing oils, such as glycerol and fatty acid alkyl esters forming during the integrated process can be selectively separated and recovered.

DETAILED DESCRIPTION OF THE DRAWING

The FIGURE is a schematic diagram illustrating one embodiment of an apparatus for an integrated process for separation and recovery of carotenoids, tocotrienols, fatty acid alkyl esters and glycerol from oils according to the method of the present invention.

DETAILED DESCRIPTION OF THE INVENTION

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of the invention may be employed in various embodiments without departing from the scope of the invention.

Carotenoids generally comprise a polyene backbone having any two of seven 9-carbon end-groups. Carotenoids can be further classified as xanthophylls, which have an oxygen molecule at each end-group, and carotenes, which have no oxygen molecules. Carotenes can be classified according to the structure of the end-groups. The chemical structures of β- and ε-end-groups of carotenoids and of α- and β-carotenes, which contain these end-groups, are shown below. α- and β-carotenes are found in palm oil. Some carotenes can be metabolized to form vitamin A by cleavage of a double-bond, such as at 15,15' position of β-carotene.

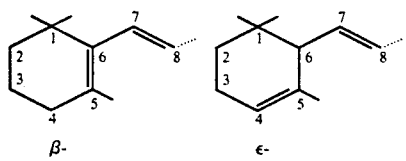

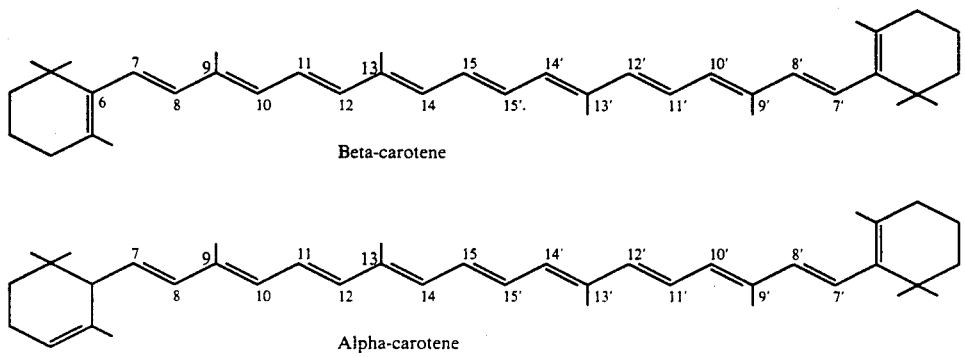

Tocotrienols are methyl-substituted chromanols containing an unsaturated three-isoprene moiety side chain. The general structure of tocotrienols can be seen below:

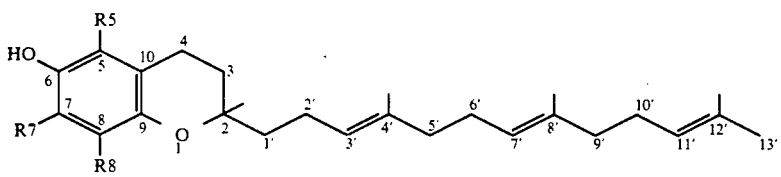

where R5, R7 and R8 are either hydrogen or methyl groups. Tocotrienols and tocopherols are homologs of vitamin E. Tocotrienols differ from tocopherols in that the three-isoprene moiety side chain contained in tocopherols is saturated with chiral carbons located at positions 2, 4' and 8', while tocotrienols have an unsaturated and unconjugated side chain at positions 3', 7' and 11'.

α-, γ- and δ-tocotrienols are classified according to the presence or absence of methyl groups at the 5, 7 and 8 positions of the chromanol group. α-tocotrienol contains methyl groups at all three positions. γ-tocotrienol contain a hydrogen group at the 5-position and methyl groups at the 7- and 8-positions. δ-tocotrienol contains hydrogen groups at the 5- and 7-positions and a methyl group at the 8-position. These tocotrienols are generally present in palm oil in the following amounts: about 205 ppm α-tocotrienol; about 439 ppm γ-tocotrienol; and about 94 ppm δ-tocotrienol. Smaller concentrations of tocotrienols can be found, for example, in sunflower oil, coconut oil and wheat germ oil.

Palm oil, which contains both carotenoids and tocotrienols, also contains the following glycerides:
linolein
$(CH_3(CH_2)_4CH:CHCH_2CH:CH(CH_2)_7COO)_3(C_3H_5)$;
tripalmitin $(CH_3(CH_2)_{14}COO)_3(C_3H_5)$;
olein $(CH_3(CH_2)_7CH:CH(CH_2)_7COO)_3(C_3H_5)$; and
stearin $(CH_3(CH_2)_{16}COO)_3(C_3H_5)$.

As can be seen, linolein and olein contain unsaturated carbon bonds. Tripalmitin and stearin contain only saturated carbon bonds.

One embodiment of the present invention, integrated process system 10, is shown in the FIGURE. Crude palm oil is directed from crude palm oil source 12 into fractionation vessel 14, having agitator 16. Although crude palm oil is preferred, other suitable oils containing carotenoids and tocotrienols can be used. Examples of other suitable oils include sunflower oil, coconut oil, wheat germ oil and carrot oil.

Materials of construction for use in integrated process system 10, unless otherwise specified, include materials suitable for use with the process of the present invention. Examples of suitable materials of construction include glass and stainless steel. Methods of directing the crude palm oil and fluid components thereof through integrated process system 10 include, for example, pumping, such as with a positive-displacement pump or centrifugal pump, not shown, and application of pressure to the fluid source by directing a suitable non-reactive gas to the fluid source, such as nitrogen gas.

Fractionation vessel 14 is cooled by a suitable cooling medium conducted through a jacket 18 at fractionation vessel 14. The cooling medium is selected to allow cooling of the crude palm oil in fractionation vessel 14 to a temperature in the range of between about −20° C. to about 5° C. An example of a suitable coolant is propylene glycol. In one embodiment, fractionation vessel 14 has a conical bottom portion 20, which is an inverted cone.

Crude palm oil in fractionation vessel 14 is exposed to a solvent under conditions sufficient to cause miscellar fractionation under conditions which obviate destruction of carotenoids and tocotrienols in the crude palm oil. During miscellar fractionation, glycerides which contain no unsaturated carbon bonds, such as stearin and tripalmitin, precipitate and are then separated from the crude palm oil. In one embodiment, a solvent is directed from solvent source 22 to fractionation vessel 14. Solvents suitable for use include those which, under suitable conditions, cause substantially all tripalmitin and stearin to precipitate. Examples of suitable solvents include hexane, acetone and ethyl acetate. In a preferred embodiment, the solvent is hexane. The amount of solvent added to the crude palm oil is in the range of between about one volume and about ten volumes of solvent per volume of the crude palm oil in fractionation vessel 14. In a preferred embodiment, about five volumes of solvent are added per volume of crude palm oil.

Suitable conditions for miscellar fractionation of the crude palm oil include agitating the crude palm oil and the solvent in fractionation vessel 14 by agitator 16 for a period of time in the range of between about one minute and about ten minutes in order to form a homogenous miscella. In a preferred embodiment, the crude palm oil and the solvent are agitated for about five minutes. Agitation is then stopped and the mixture is exposed to conditions sufficient to cause substantially all saturated glycerides, such as tripalmitin and stearin, contained in the crude palm oil to precipitate from the crude palm oil. In one embodiment sufficient conditions include maintaining the temperature of the crude palm oil and solvent in the range of between about $-20°$ C. and about $5°$ C. for a period of time in the range of between about five hours and about twenty hours to cause a lower saturated glyceride layer and an upper crude palm oil layer to form. The lower saturated glyceride layer contains hexane and substantially all precipitated saturated glycerides. The upper crude palm oil layer contains solvent and the remainder of the crude palm oil components.

The lower saturated glyceride layer and the upper crude palm oil layer are then separated, such as by directing the lower saturated glyceride layer from fractionation vessel 14 through a suitable filter 24 for substantially retaining precipitated saturated glycerides in filter 24 and thereby forming a filtrate. Conical bottom portion 20 of fractionation vessel 14 operates by reducing surface area between the lower saturated glyceride layer and the upper crude palm oil layer, thereby increasing separation of the lower saturated glyceride layer from the upper crude palm oil while the lower solvent layer is being fractionation vessel 14 to filter 24. The filtrate is collected from filter 24 in filtrate vessel 26. Examples of a suitable filter include a vacuum filter and a centrifuge. A suitable filer media is cheesecloth. Saturated glyceride precipitate collected on filter 24 is then washed with a solvent wash directed from solvent source 22 through filter 24 and then to filtrate vessel 26 to thereby remove residual carotenoids from the saturated glyceride precipitate. The amount of solvent wash employed is in the range of between about 0.2 volumes and about two volumes per volume of crude palm oil directed from crude palm oil source 12 to fractionation vessel 14. The solvent wash is combined in filtrate vessel 26 with the filtrate.

The solvent wash and filtrate can then be vacuum evaporated under conditions sufficient to substantially remove the solvent. In one embodiment, the collected solvent and filtrate are directed from filtrate vessel 26 to vacuum evaporator 28. The solvent in the solvent wash and filtrate is evaporated in evaporator 28 at an absolute pressure in the range of between about fifteen mm Hg and about thirty mm Hg at a temperature in the range of between about $35°$ C. and about $45°$ C. when the solvent form solvent source 22 comprises hexane, for example. Carotenoids remaining in vacuum evaporator 28 following removal of the solvent can be returned to the crude palm oil layer in fractionation vessel 14.

The crude palm oil layer in fractionation vessel 14 is directed from fractionation vessel 14 to esterification vessel 30, having agitator 32, for alcoholic esterification. It is to be understood, however, that crude palm oil can be directed from crude palm oil source 12 to esterification vessel 30 for alcoholic esterification therein without having been exposed to miscellar fractionation. Esterification vessel 30 can have a bottom portion 34 which is an inverted cone.

Alcoholic esterification includes reaction of the triglycerides in the crude palm oil or crude palm oil layer with a lower alkyl alcohol in the presence of a base. Ester bonds of the glycerides are cleaved by this reaction, thereby forming glycerides and fatty acid alkyl esters. An example of this reaction is shown below:

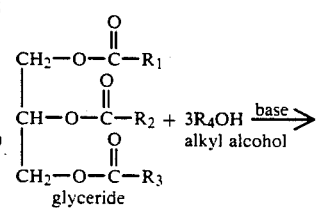

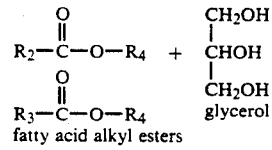

Where crude palm oil is subjected to alcoholic esterification, the glycerides can include tripalmitin, stearin, olein and linolein. $R_1$, $R_2$ and $R_3$ represent saturated and unsaturated carbon chains corresponding to fatty acids of a group including palmitic acid, oleic acid, stearic acid and linoleic acid. $R_4$ represents the carbon chain of the alcohol reacted with the glycerides. The fatty acid alkyl esters produced by the reaction include alkyl esters of the following fatty acids:

linoleic acid $(CH_3(CH_2)_4CH{:}CHCH_2CH{:}CH(CH_2)_7COOH)$;
palmitic acid $(CH_3(CH_2)_{14}COOH)$;
oleic acid $(CH_3(CH_2)_7CH{:}CH(CH_2)_7COOH)$; and
stearic acid $(CH_3(CH_2)_{16}COOH)$.

In one embodiment of the present invention, alcoholic esterification of glycerides includes directing an esterification solution, comprising a base and a lower alkyl alcohol, from esterification solution source 36 to esterification vessel 30. Lower alkyl alcohol, as that term is used herein, means alcohols having saturated carbon chains including between about one carbon and four carbons. Examples of lower alkyl alcohols include methanol, ethanol, isopropanol and butanol. The lower alkyl alcohol is suitable for alcoholic esterification of the glycerides in the crude palm oil under suitable conditions. In a preferred embodiment, the lower alkyl alcohol comprises methanol. In a preferred embodiment, the base comprises sodium hydroxide, present in the esterification solution in an amount sufficient to cause alcoholic esterification of the glycerides in the crude palm oil layer under suitable conditions. Alternatively, potassium hydroxide can be employed to cause sub alcoholic esterification. In one embodiment, sodium hydroxide comprises between about 0.1 weight percent and about three weight-percent per volume of the esterification solution. In a particularly preferred embodiments, the concentration of the sodium hydroxide is between about 0.1 weight percent and about two weight percent per volume of the esterification solution.

Enough esterification solution is directed from esterification solution source 36 to combine with the crude palm oil layer in esterification vessel 30 to cause alcoholic esterification of the glycerides in the crude palm oil layer under suitable conditions. In one preferred embodiment, between about 0.2 gram and about one gram of esterification solution per gram of crude palm oil layer are combined with the crude palm oil layer. In a particularly preferred embodiment, about 0.33 gram of esterification solution are combined with each gram of crude palm oil layer in esterification vessel 30.

The esterification solution in esterification vessel 30 is contacted with the crude palm oil under conditions sufficient to form a reaction mixture wherein the glycerides in the crude palm oil layer substantially react to form glycerol and fatty acid alkyl esters. In one embodiment, sufficient conditions for reaction of the glycerides includes agitation by an agitator 32 of the reaction mixture at a temperature in the range of between about 35° C. and about 50° C. Agitation of the reaction mixture is continued for a period of time in the range of between about four hours and about sixteen hours. In another embodiment, agitation is conducted at a temperature in the range of between about 50° C. and about 70° C. for a period of time int he range of between about 0.5 hour and about four hours. In a particularly preferred embodiment, the reaction mixture is agitated at a temperature of about 60° C. for a period of time of about 0.5 hour.

Following the period of agitation, the reaction mixture is allowed to settle under conditions sufficient to cause an upper ester-rich layer and a lower glycerol-rich layer to form. In one embodiment, the upper ester-rich layer and the lower glycerol-rich layer are allowed to settle for a period of time greater than about ten minutes at a temperature in the range of between about 10° C. and about 40° C. The upper ester-rich layer contains a substantial portion of the fatty acid alkyl esters formed during alcoholic esterification, the carotenoids and the tocotrienols contained in the crude palm oil layer. The lower glycerol-rich layer contains a substantial portion of the glycerols formed during alcoholic esterification. The ester-rich layer is the upper layer because the methanol and fatty acid alkyl esters contained in the ester-rich layer are less dense than water generated during the alcoholic esterification, which is contained in the glycerol-rich layer.

The lower glycerol-rich layer is then separated from the upper ester-rich layer. In one embodiment, the lower glycerol-rich layer can be separated from the ester-rich layer by directing the glycerol-rich layer from esterification vessel 30 to neutralization vessel 40. Bottom portion 34 of esterification vessel 30 operates by decreasing the surface area between the lower glycerol-rich layer and the upper ester-rich layer, thereby increasing separation of the glycerol-rich layer from the ester-rich layer while the glycerol-rich layer is being directed from esterification vessel 30 to neutralization vessel 40.

Water is then directed from water source 44 into esterification vessel 30 in an amount sufficient to substantially remove base remaining in the ester-rich layer. In a preferred embodiment, about five volumes of water per volume of ester-rich layer are directed into esterification vessel 30. It is to be understood, however, that more than five volumes of water layer per volume of ester-rich layer can be directed into esterification vessel 30. The ester-rich layer and water in esterification vessel 30 are agitated by agitator 32 for a period of time of less than than about two minutes at a temperature in the range of between about 20° C. and about 35° C. Following agitation, the ester-rich layer and the water layer are settled for a period of time in the range of between about one minute and about two hours. A lower water layer containing base from the ester-rich layer is thereby formed. The water layer is separated from the ester-rich layer by directing the lower water layer from esterification vessel 30 to the glycerol-rich layer in neutralization vessel 40.

The ester-rich layer is then directed from esterification vessel 30 to solvolytic micellization vessel 46 for solvolytic micellization. First solvolytic micellization vessel 46 includes conical bottom portion 48. Solvolytic micellization, as that term is used herein, means combining the ester-rich layer with a lower alkyl alcohol under conditions sufficient to form carotenoid micelles of carotenoids in the ester-rich layer. Carotenoid micelles comprise regions of carotenoids around which a single, or mono, layer of fatty acid alkyl esters is formed. These carotenoid micelles are suspended by the ester-rich layer in which they are formed. Carotenoid micelles form because the fatty acid portion of the fatty acid alkyl esters are relatively soluble in the carotenoid micelles compared to the methanol in the ester-rich layer, while the ester portion of the fatty acid alkyl esters have a greater solubility in the methanol in the ester-rich layer. Water is then added to diminish the solubility of the fatty acid alkyl esters in the ester-rich layer, thereby causing the carotenoid micelles to combine and form a lower carotenoid-rich layer. Alternatively, a solution of a suitable lower alkyl alcohol and water can be combined with the ester-rich layer to form an upper ester-rich layer and a lower carotenoid-rich layer.

In a preferred embodiment, the ester-rich layer is contacted with a lower alkyl alcohol and thereafter contacted with water under conditions sufficient to cause solvolytic micellization of the ester-rich layer without destroying the carotenoids and the tocotrienols contained in the ester-rich layer. Examples of suitable lower alkyl alcohols for solvolytic micellation include methanol, ethanol, propanol, butanol, etc. In a preferred embodiment, the lower alkyl alcohol comprises methanol. The lower alkyl alcohol can be combined with water in an amount less than about five percent of water by volume. The methanol is directed from lower alkyl alcohol source vessel 50 to solvolytic micellization vessel 46 containing the ester-rich layer. The amount of lower alkyl alcohol directed from lower alkyl alcohol source 50 to first solvolytic micellization vessel 46 is in the range of between about three volumes and about ten volumes per volume of ester-rich layer contained in first solvolytic micellization vessel 46. Preferably, about five volumes of methanol per volume of ester-rich layer are added to first solvolytic micellization vessel 46 and contacted with the ester-rich layer. The methanol and ester-rich layer are then agitated by a suitable means, such as by an agitator, not shown, under conditions sufficient to cause the carotenoids and fatty acid alkyl esters contained in the ester-rich layer to form micelles. In one embodiment, sufficient conditions to form micelles include agitating the ester-rich layer and methanol for a period of time less than about two minutes at a temperature in the range of between about 20° C. and about 60° C.

Following agitation, a sufficient amount of water is added to the ester-rich layer to significantly diminish the solubility of the fatty acid alkyl esters in the ester-rich layer, thereby causing the carotenoid micelles to combine to form a lower carotenoid-rich layer. The water is directed from water source 52 to first solvolytic micellization vessel 46 in an amount sufficient to cause a lower immiscible carotenoid-rich layer to form. The carotenoid-rich layer is the lower layer because it is more dense than the ester-rich layer, which contains the methanol. In one embodiment, a sufficient amount of water is an amount of water in the range of between about one percent and about six percent of the total volume of methanol combined with the ester-rich layer in first solvolytic micellization vessel 46. Carotenoids are thereby substantially removed from the ester-rich layer.

Alternatively, solvolytic micellization can be conducted without adding water after combining methanol with the ester-rich layer. In this alternative embodiment, an upper ester-rich layer and a lower carotenoid-rich layer can be formed by combining the ester-rich layer with between about three volumes an about ten volumes of methanol having a concentration of water in the range of between about one percent and about six percent by volume of water. In a preferred embodiment, about five volumes of methanol containing about three percent water are combined with the ester-rich layer to obtain a lower carotenoid-rich layer.

The lower carotenoid-rich layer contains a substantial portion of the carotenoids which were in the ester-rich layer prior to solvolytic micellization. The carotenoid-rich layer also contains lesser portions of the tocotrienols and the fatty acid alkyl esters which were contained in the ester-rich layer prior to solvolytic micellization of the ester-rich layer. The upper ester-rich layer contains a substantial portion of the tocotrienols which were contained in the ester-rich layer prior to solvolytic micellization. A substantial portion of fatty acid alkyl esters remain in the ester-rich layer because the ester layer has a greater volume than the carotenoid-rich layer formed by solvolytic micellization. In addition to tocotrienols and fatty acid alkyl esters, the ester-rich layer contains a lesser portion of carotenoids.

The carotenoid-rich layer is then separated from the ester-rich layer. In one embodiment, the carotenoid-rich layer is separated from the ester-rich layer by directing the carotenoid-rich layer from first solvolytic micellization vessel 46 to second solvolytic micellization vessel 54 having conical bottom portion 56. Conical bottom portion 48 of first solvolytic micellization vessel 46 operates by decreasing the surface area between the upper ester-rich layer and the lower carotenoid-rich layer during direction of the carotenoid-rich layer to second solvolytic micellization vessel 54, thereby increasing separation of the ester-rich layer from the carotenoid-rich layer. The ester-rich layer is then directed from first solvolytic micellization vessel 46 to ester-rich layer collection vessel 58. In a preferred embodiment, the temperature of ester-rich layers collected in the ester-rich layer collection vessel 58 is maintained in the range of between about 20° C. and about 60° C.

A second solvolytic micellization is conducted employing the carotenoid-rich layer in second solvolytic micellization vessel 54. Solvolytic micellization is repeated by exposing the carotenoid-rich layer in second solvolytic micellization vessel 54 to conditions similar to the first solvolytic micellization of the ester-rich layer. The concentration of carotenoids in the carotenoid-rich layer are increased during the second solvolytic micellization, thereby forming a preferential path for carotenoids in integrated process system 10. The lower alkyl alcohol employed is the same as that employed in the first solvolytic micellization. For example, in a preferred embodiment, methanol would be used for the second solvolytic micellization if methanol had also been used during the first solvolytic micellization.

The second solvolytic micellization includes directing methanol, in an amount in the range of between about three volumes and about ten volumes per volume of carotenoid-rich layer, from lower alkyl alcohol source vessel 50 to second solvolytic micellization vessel 54 and combining the methanol with the carotenoid-rich layer contained therein. In one preferred embodiment, about five volumes of methanol per volume of carotenoid-rich layer are employed. The combined methanol and carotenoid-rich layer are then agitated by a suitable means and under the same conditions as were the methanol and ester-rich layer in first solvolytic micellization vessel 46, thereby forming a colloidal suspension of micelles in the carotenoid-rich layer.

Following agitation, water is directed from water source 52 to second solvolytic micellization vessel 54 in an amount in the range of between about one percent and about six percent by volume of the total amount of methanol combined with the carotenoid-rich layer. An upper solvent layer is formed by the addition of water to the micelles and carotenoid-rich layer. The upper solvent layer contains a substantial portion of the tocotrienols and the fatty acid alkyl esters which were contained in the carotenoid-rich layer when the carotenoid-rich layer was transferred to second solvolytic micellization vessel 54. The carotenoids are substantially retained in the lower carotenoid-rich layer. The lower carotenoid-rich layer is then transferred from second solvolytic micellization vessel 54 to third solvolytic micellation vessel 60, having conical bottom portion 62. Conical bottom portion 56 of second solvolytic micellization vessel 60 operates to improve separation of the carotenoid-rich layer and the solvent layer in the same manner as bottom portion 48 operated to improve separation of the upper ester-rich layer and lower carotenoid-rich layer following the first solvolytic micellization. The upper solvent layer is then directed from second solvolytic micellization vessel 54 to ester-rich layer collection vessel 58 and combined with the ester-rich layer contained therein.

A third solvolytic micellization of the carotenoid-rich layer is conducted in third solvoytic micellization vessel 60. The lower alkyl alcohol, which comprises methanol in this embodiment, is combined with the carotenoid-rich layer in amounts proportional to the amounts employed in the second solvolytic micellization. The combined methanol and carotenoid-rich layer are then agitated by a suitable means and under the same conditions as were the methanol and carotenoid-rich layer in second solvolytic micellization vessel 54. Micelles are formed by the addition of methanol and agitation of the carotenoid-rich layer.

Following agitation, water is directed from water source 52 to third solvolytic micellization vessel 60 in an amount in the range of between about one percent and about six percent of the total amount of methanol combined with the carotenoid-rich layer in third solvolytic micellization vessel 60. An upper solvent layer and a lower carotenoid-rich layer are formed by the addition of water to the colloidal suspension of micelles. The lower carotenoid-rich layer is then separated from the upper solvent layer. The carotenoid-rich layer formed is directed from third solvolytic micellization vessel 60 to fourth solvolytic micellization vessel 64, having conical bottom portion 66. The solvent layer formed is directed from third solvolytic micellization vessel 60 to ester-rich layer collection vessel 58.

A fourth solvolytic micellization is conducted in fourth solvolytic micellization vessel 64 employing the carotenoid-rich layer formed in third solvolytic micellization vessel 60. Methanol and water are added to the carotenoid-rich layer in third solvolytic micellization vessel 60 in volumes proportionate to the volumes of methanol and water employed during the third solvolytic micellization. The lower carotenoid-rich layer and the upper solvent layer formed during the fourth solvolytic micellization are then separated. In one embodiment, the lower carotenoid-rich layer is directed from fourth solvolytic micellization vessel 64 to carotenoid-rich layer evaporator 68. The solvent layer formed is then directed from fourth solvolytic micellization vessel 64 to ester-rich layer collection vessel 58 and combined with the solvent layers and with the ester-rich layer therein. The ester-rich layer and the solvent layers form a single collective ester-rich layer. The collective ester-rich layer contains a substantial portion of of the fatty acid alkyl esters and tocotrienols which were contained in the ester-rich layer prior to solvolytic micellization. The collective ester-rich layer can also contains lesser portions of carotenoids which were in the ester-rich layer prior to solvolytic micellization. The carotenoid-rich layer contains a substantial portion of the carotenoids which were contained in the crude palm oil layer.

Following the solvolytic micellizations, the carotenoid-rich layer can be exposed to conditions sufficient to remove relatively volatile components, such as residual water and lower alkyl alcohol present. In one embodiment, relatively volatile components of the carotenoid-rich layer are removed from the carotenoid-rich layer in carotenoid-rich layer evaporator 68. In a preferred embodiment, the lower alkyl alcohol and water are vacuum evaporated in carotenoid-rich layer evaporator 68 at a temperature in the range of between about 20° C. and about 65° C. and at an absolute pressure in the range of between about one mm Hg and about ten mm Hg. An example of a suitable carotenoid-rich layer evaporator 68 is a Buchi 461 model rotavaporizer, commercially available from Brinkman, Inc. Alternatively, the carotenoid-rich layer in fourth solvolytic micellization vessel 64 can be directed from fourth solvolytic micellization vessel 64 to saponification vessel 70 without being exposed to vacuum evaporation.

In a preferred embodiment, the carotenoid-rich layer is directed from carotenoid-rich layer evaporator 68 to saponification vessel 70. Fatty acid alkyl esters contained in the carotenoid-rich layer are saponified by reacting the fatty acid alkyl esters with a suitable base solution. In one embodiment, the base solution is a solution of a lower alkyl alcohol and a base. In a preferred embodiment, the lower alkyl alcohol comprises methanol and the base comprises potassium hydroxide. The solution contains base in the amount of between about eight percent by weight and about seventeen percent by weight. In a particularly preferred embodiment, the base solution contains about seventeen percent by weight of base. It is to be understood, however, that the base can comprise sodium hydroxide. The base solution can be formed in base solution source vessel 72, which is constructed of a suitable material for contact with the base solution. An example of a suitable material is stainless steel. The base solution is directed from base source vessel 72 to carotenoid-rich layer in saponification vessel 70 to form a reaction mixture. An amount of base solution is directed into saponification vessel 70 sufficient to create a molar excess of base in the range of between about two times and about four times the stoichiometric amount of base required to saponify the fatty acid alkyl esters contained in the reaction mixture.

The base and the fatty acid alkyl esters in the reaction mixture are exposed to conditions sufficient to cause the fatty acid alkyl esters to form fatty acid salts which are insoluble in the reaction mixture. The empirical formula for the saponification reaction is:

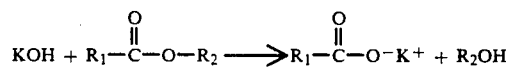

where $R_1$ and $R_2$ are carbon chains of the fatty acid alkyl esters.

Conditions sufficient to cause the saponification reaction include agitating the reaction mixture by a suitable means, such as by an agitator, not shown, and maintaining the temperature of the reaction mixture in the range of between about 25° C. and about 80° C. The period of time of agitation is in the range of between about thirty minutes and about twelve hours. In a preferred embodiment, the base solution and the carotenoid-rich layer are maintained at a temperature of about 56° C. for a period of time of about thirty minutes to thereby saponify the fatty acid alkyl esters in the carotenoid-rich layer.

Following the saponification reaction, the carotenoids are extracted from the reaction mixture. In one embodiment, the carotenoids are extracted by directing the reaction mixture from saponification vessel 70 to first extraction vessel 74. A suitable extraction solvent is then directed from extraction solvent source 76 to first extraction vessel 74. Examples of suitable extraction solvents include medium-length chain hydrocarbons containing carbon chains having between about five carbons and about eight carbons. Examples of suitable extraction solvents include hexane, heptane, petroleum ether, etc. In a particularly preferred embodiment, the extraction solvent comprises petroleum ether.

A sufficient amount of extraction solvent is added to the reaction mixture to extract a substantial portion of the carotenoids from the reaction mixture. In one embodiment, between about one and four extractions is conducted to extract the carotenoids from the reaction mixture. Each extraction employs extraction solvent in an amount between about one-fifth and about one-half the volume of the reaction mixture. In a preferred embodiment, the volume of petroleum ether employed for each extraction is about one-half the volume of the reaction mixture in first extraction vessel 74. In a particularly preferred embodiment, the temperature of the reaction mixture and the extraction solvent during each extraction is in the range of between about 10° C. and about 40° C.

The extraction solvent and the reaction mixture during the first extraction are agitated by a suitable means, such as by an agitator, not shown, for a period of time in the range of between about one minute and about five minutes. The extraction solvent and the reaction mixture are then settled for a period of time in the range of between about one minute and about ten minutes. During agitation, carotenoids in the reaction mixture are transported from the reaction mixture to the extraction solvent. During settling of the reaction mixture and the extraction solvent, an upper solvent layer and a lower reaction mixture layer form.

The upper solvent layer contains the extraction solvent, a small amount of base and a substantial portion of the carotenoids which were contained in the reaction mixture. The lower reaction mixture layer is separated from the upper solvent layer by directing the lower reaction mixture layer from first extraction vessel 74 to second extraction vessel 78. First extraction vessel 74 can have a conical bottom portion, not shown, to improve separation of the lower reaction mixture layer from the upper solvent layer. The upper solvent layer is then directed from first extraction vessel 74 to solvent layer collection vessel 80.

Extraction solvent is directed from extraction solvent source 76 to second extraction vessel 78 and combined with the reaction mixture for a second extraction. The reaction mixture and the extraction solvent are agitated by a suitable means, such as by an agitator, not shown, and then settled. The periods of time for agitation and settling of the reaction mixture and solvent are the same as the periods of time suitable for agitating and settling during the first extraction. An upper solvent layer is thereby formed, containing a substantial portion of the carotenoids which were contained in the reaction mixture layer following the first extraction. The lower reaction mixture layer is then separated from the upper solvent layer by directing the lower solvent layer from second extraction vessel 78 to third extraction vessel 80. Second extraction vessel 78 can have a control bottom portion, not shown, to improve separation of the lower reaction mixture layer from the upper solvent layer. The upper solvent layer is then directed from second extraction vessel 78 to solvent layer collection vessel 80 and combined with the solvent layer formed during the first extraction.

A third extraction is conducted in third extraction vessel 82 in the same manner as the first and second extractions. The resulting lower reaction mixture layer is separated from the upper solvent layer by directing the lower reaction mixture layer from third extraction vessel 82 to fourth extraction vessel 84. Third extraction vessel 82 can have a conical bottom portion, not shown, for improving the separation. The resulting upper solvent layer is directed from third extraction vessel 82 to solvent layer collection vessel 80 and combined with the solvent layers of the first and second extraction.

A fourth extraction is conducted in fourth extraction vessel 84 in the same manner as the first three extractions. Fourth extraction vessel 84 can have a conical bottom portion, not shown, for improving the separation. The resulting lower reaction mixture layer is discarded. The resulting upper solvent layer containing carotenoids is directed from fourth extraction vessel 84 to solvent layer collection vessel 80 and combined with the solvent layers of the previous extractions.

The collected solvent layers in solvent layer collection vessel 80 form a single solvent layer containing a substantial portion of the carotenoids and tocotrienols which were contained int he reaction mixture. Also contained in the solvent layer are lesser portions of fatty acid alkyl esters which were not saponified during the saponification reaction. The solvent layer is washed with a suitable solvent solution or salt solution for removing base from the solvent layer. An example of a suitable salt solution is 1.5M sodium chloride solution. In one embodiment, a volume of 1.5M sodium chloride wash solution is directed from wash solution source vessel 86 into solvent layer wash vessel 80 and combined with the solvent layer. The wash solution and the solvent layer are agitated by a suitable means, such as by an agitator, not shown, for a period of time in the range of between about one minute and about five minutes and at a temperature in the range of between about 20° C. and about 40° C. In a preferred embodiment, the wash solution and the solvent layer are agitated for about two minutes at a temperature of about 25° C.

During agitation, base in the solvent layer is washed from the solvent layer to the wash solution. The solvent layer and the wash solution are allowed to settle after agitation for a period of time in the range of between about one minute and about ten minutes and at a temperature in the range of between about 20° C. and about 40° C. In a preferred embodiment, the wash solution and the solvent layer are allowed to settle for about five minutes at a temperature of about 25° C. During settling of the wash solution and solvent layer, a lower layer of the wash solution forms containing a substantial portion of the base which was contained in the solvent layer prior to washing with the wash solution. The upper solvent layer contains a substantial portion of the carotenoids which were contained in the crude palm oil. The lower layer is directed from the solvent layer collection vessel 80 and discarded. The wash of the solvent layer can be repeated using successive volumes of wash solution equal to the first wash solution. In a preferred embodiment, the solvent layer is washed about five times.

Following washing of the solvent layer in solvent layer collection vessel 80, the solvent layer is exposed to conditions sufficient to substantially remove the solvent from the solvent layer, thereby forming a carotenoid-rich paste containing a substantial portion of the carotenoids which were contained in the crude palm oil. In one embodiment, the solvent in the solvent layer is directed from solvent layer collection vessel 80 to solvent layer evaporator 88. It is to be understood, however, that the ester-rich layer can be directed from esterification vessel 30 to solvent layer evaporator 88 for individual separation of carotenoids without first conducting solvolytic micellization.

Conditions sufficient to substantially remove the solvent can include exposing the solvent layer in solvent layer evaporator 88 to an absolute pressure of between about ten mm Hg and about forty mm Hg while maintaining the temperature of the solvent layer in the range of between about 25° C. and about 55° C. In a preferred embodiment, the solvent is vacuum evaporated in a suitable rotavaporizer at an absolute pressure of about twenty-five mm Hg and at a temperature of about 30° C.

An example of a suitable rotavaporizer is a Buchi 461 model rotavaporizer.

When evaporation of solvent from the collected solvent layer is complete, the resulting carotenoid-rich paste containing the carotenoids can be dried to remove remaining solvent which did not evaporate. In one embodiment, the carotenoid-rich paste is dried by exposing the carotenoid-rich paste to nitrogen gas which is flowed from nitrogen source 90 across the carotenoid-rich paste at a suitable rate. Nitrogen source 90 can be a cylinder or some other suitable source. The temperature of the carotenoid-rich paste and of the nitrogen gas is in the range of between about 20° C. and about 30° C. The pressure of the nitrogen gas as it is flowed across the carotenoid-rich paste is about atmospheric. The carotenoid-rich paste is dried for a period of time in the range of between about five minutes and about thirty minutes or until there is essentially no solvent in the paste. In one embodiment, the carotenoid-rich paste contains between about ten percent and about thirty percent by weight of carotenoids and between about seventy percent and about ninety percent by weight of fatty acid alkyl esters which were not saponified during reaction with the base in saponification vessel 70. The carotenoid-rich paste is then directed from solvent layer evaporator 88 to carotenoid recovery vessel 92 manually or by some other suitable means. The carotenoid-rich paste contains a substantial portion of the carotenoids, tocotrienols and fatty acid alkyl esters present in the solvent layer directed into solvent layer evaporator 88.

Individual carotenoids can be adsorptively separated. In one embodiment, carotenoid-rich layer from which lower alkyl alcohol and water have been evaporated is directed from carotenoid-rich layer evaporator 68 to carotenoid recovery vessel 92. Carotenoid recovery vessel 92 is suitable for separating carotenoids in the carotenoid-rich layer. In a preferred embodiment, carotenoid recovery vessel 92 has a length of between about ten centimeters and about fifty centimeters and an internal diameter of between about one centimeter and about five centimeters. Carotenoid recovery vessel 92 is packed with a suitable adsorbent 94. Examples of suitable adsorbents include alumina, silica gel, silicic acid, magnesium oxide, calcium hydroxide, magnesium hydroxide, powdered sugar and cellulose. In a particularly preferred embodiment, the adsorbent comprises alumina ($Al_2O_3$), AG 7 100/200 mesh grade packing, commercially available from BioRad, Inc. The volume of adsorbent 94 in carotenoid recovery vessel 92 is sufficient to substantially adsorb the carotenoid-rich layer directed into carotenoid recovery vessel 92. In one embodiment, the weight of adsorbent 94 is in the range of between about two grams and about twenty grams per gram of carotenoid-rich layer. The adsorbent is wet-packed in the carotenoid recovery vessel 92 with a suitable solvent to prevent irregular elution caused by the presence of air bubbles in carotenoid recovery vessel 92. An example of a suitable solvent in which the adsorbent is wet-packed is hexane. In a preferred embodiment, about ten grams of adsorbent 94 per gram of carotenoid-rich layer is contained in carotenoid recovery vessel 92 and the adsorbent is wet-packed in about five milliliters of hexane per gram of adsorbent.

The carotenoid-rich layer is directed into the top of carotenoid recovery vessel 92 by a suitable method, such as by gravity feed and contacted with adsorbent 94. Fatty acid alkyl esters in the carotenoid-rich paste are then eluted from adsorbent 94 in carotenoid recovery vessel 92 by contacting adsorbent 94 with a suitable eluant under suitable conditions. Suitable eluants include medium-length chain hydrocarbons, such as hexane, heptane, petroleum ether, etc. Suitable conditions include a temperature in the range of between about 20° C. and about 27° C. and addition of the solvent to carotenoid recovery vessel 92 over a period of time in the range of between about one hour and about four hours. In a preferred embodiment, the fatty acid alkyl esters are eluted by directing hexane from hexane source 96 through carotenoid recovery vessel 92 and across adsorbent 94 by gravity at a temperature of about 25° C. The eluant containing fatty acid alkyl esters eluted from adsorbent 94 is collected in receptacle 98 as an eluate fraction. In a preferred embodiment, the solvent is hexane. Sufficient hexane is directed from hexane source 96 through carotenoid-rich layer recovery vessel 92 to substantially elute fatty acid alkyl esters from adsorbent 94. In a preferred embodiment, the total volume of hexane used to elute the fatty acid alkyl esters is in the range of between about five volumes and about twenty volumes per volume of carotenoid-rich paste.

Carotenoids adsorbed by adsorbent 94 are then separated and eluted from the carotenoid recovery vessel 92 by directing a suitable eluant into the top of carotenoid recovery vessel 92 by a suitable method, such as by gravity feed, and contacting the solvent solution with adsorbent 94 and the adsorbed carotenoid-rich paste contained therein. In one embodiment, the eluant comprises an eluant admixture of a suitable medium-length chain hydrocarbon and a lower alkyl alcohol. Medium-length chain hydrocarbons include, for example, hexane, heptane, petroleum ether, etc. Examples of suitable lower alkyl alcohols include methanol, ethanol, isopropanol, butanol, etc. In a particularly preferred embodiment, the eluant admixture contains isopropanol in the range of between about one percent and about fifteen percent by volume and hexane in the range of between about eighty-five percent and about ninety-nine percent by volume. The eluant admixture is prepared by suitably combining, such as by agitation, hexane from hexane source 96 and isopropanol from isopropanol source 100 in eluant admixing vessel 102.

The eluant admixture is directed from eluant admixing vessel 102 to carotenoid recovery vessel 92 in an amount sufficient to substantially separate adsorbed carotenoids contained in the carotenoid-rich paste. In one embodiment, the total volume of eluant admixture employed to separate and elute the carotenoids is in the range of between about two volumes and about twenty volumes per volume of the carotenoid-rich layer, unconcentrated by vacuum evaporation. In a preferred embodiment, the volume of eluant admixture is about five times greater than that of the adsorbed carotenoid-rich layer.

In a preferred embodiment, the amount of isopropanol relative to hexane in the eluant admixture is increased as carotenoids are eluted from carotenoid recovery vessel 92. The concentration of isopropanol can be increased either continuously or incrementally. In a particularly preferred embodiment, the increase in concentration of lower alkyl alcohol in the eluant admixture is obtained in two percent increments from about one percent to about fifteen percent lower alkyl alcohol by volume of eluant admixture during elution of carotenoids from carotenoid recovery vessel 92.

Carotenoids are eluted from the carotenoid recovery vessel 92 and are collected in clean and empty receptacle 98. The first fraction of carotenoids eluted form the column is β-carotene and a lesser amount of α-carotene. A second fraction contains α-carotene and a lesser amount of β-carotene. Lycopene and xanthophylls are eluted after α- and β-carotene have been eluted from carotenoid recovery vessel 92.

Eluate fractions containing α- and β-carotenes can be directed separately from carotenoid recovery vessel 92 to refined recovery vessel 104, containing adsorbent 106, for further separating the α- and β-carotenes. Adsorbents, wet-packing solvent and admixtures which are suitable for use in carotenoid recovery vessel 92 are also suitable for use in refined carotenoid recovery vessel 104. Sufficient eluant admixture is directed from eluant admixture vessel 102 into refined carotenoid recovery vessel 104 to elute adsorbed α- and β-carotenes. Elution of α- and β-carotenes from refined carotenoid recovery vessel 104 further separates the α- and β-carotenes. The α- and β-carotenes are collected as eluate fractions in receptacle 108.

Eluant in the eluate fractions collected from carotenoid recovery vessel 92 and containing the separated fatty acid alkyl esters, carotenoids and tocotrienols is then removed from the eluate fractions. Also, eluant in the eluate fractions collected from refined carotenoid recovery vessel 104 is then removed. In one embodiment, the eluant in the eluate fraction is evaporated, such as by vacuum evaporation in vacuum evaporator 110, wherein the temperature is maintained in the range of between about 20° C. and about 45° C., and wherein the absolute pressure is maintained in the range of between about ten mm Hg and about thirty-five mm Hg during evaporation and removal of the eluant. An example of a suitable vacuum evaporator is a rotavaporizer of the type used for vacuum evaporation of the carotenoid-rich layer. The rotavaporized eluate fractions each contain individually separated fatty acid alkyl ester, α-carotenes and β-carotenes. Rotavaporized eluate fractions of the carotenoids such as Lycopene and xanthophylls can also be formed.

Following elution of components of the carotenoid-rich layer to be recovered, adsorbent 94 and adsorbent 106, in the carotenoid recovery vessel 92 and refined carotenoid recovery vessel 104, respectively, can be regenerated for reuse. However, regeneration of adsorbent 94 and adsorbent 106 is not required after each elution. In one embodiment, the adsorbent 94 and adsorbent 106 is regenerated by contacting the adsorbent with a suitable solvent in an amount sufficient to substantially remove remaining components of the carotenoid-rich layer from the adsorbent. An example of a suitable solvent includes methanol. In one embodiment, the amount of solvent employed is in the range of between about one volume and about ten volumes per volume of carotenoid-rich paste introduced to carotenoid recovery vessel 92 and refined carotenoid recovery vessel 104.

The lower alkyl alcohol and water contained in the ester-rich layer in ester-rich layer collection vessel 58 are substantially removed therefrom by exposing the ester-rich layer to conditions sufficient to remove the lower alkyl alcohol and water without destroying the tocotrienols contained in the ester-rich layer. Enough of the lower alkyl alcohol and water are removed to allow fatty acid alkyl esters to be recovered from the ester-rich layer under conditions sufficient to prevent destruction of tocotrienols contained in the ester-rich layer. It is to be understood, however, that the ester-rich layer can be directed from esterification vessel 30 to ester-rich layer collection vessel 58 without solvolytic micellization.

In a preferred embodiment, the lower alkyl alcohol and water are removed by vacuum evaporation of the water from the ester-rich layer obtained by solvolytic micellization. In a preferred embodiment, the lower alkyl alcohol comprises methanol. The ester-rich layer is directed from ester-rich layer collection vessel 58 to the bottom of ester-rich layer evaporator 112. The bottom of ester-rich layer evaporator 112 is maintained at a temperature in the range of between about 35° C. and about 50° C. and at an absolute pressure within ester-rich layer evaporator 112 in the range of between about ten mm Hg and about one hundred mm Hg. An example of a suitable ester-rich layer evaporator 112 is a rotavaporizer, such as Buchi 461 model rotavaporizer. In a preferred embodiment, the methanol and water evaporate from the ester-rich layer while the ester-rich layer is fed to ester-rich layer evaporator 112 in a continuous feed manner. Evaporation of the methanol and water in ester-rich layer evaporator 112 is continued for a period of time sufficient to substantially remove the methanol and water from the ester-rich layer.

Methanol and water evaporated from the ester-rich layer are condensed under suitable conditions in condenser 114 and then directed to lower alkyl alcohol holding vessel 116. The methanol can then be recovered, wherein the methanol is separated from the water. In one embodiment, the methanol and water can then be directed from lower alkyl alcohol holding vessel 116 to alcohol distillation column 118. The methanol is suitably distilled in alcohol distillation column 118 and thereby separated from the water. The methanol is then condensed in lower alkyl alcohol condenser 120 and collected in lower alkyl alcohol source vessel 50. The distilled methanol can be reused for use in subsequent solvolytic micellization.

Following separation of the methanol and water from the ester-rich layer, substantially all of the fatty acid alkyl esters are separated from the remaining ester-rich layer. In one embodiment, the ester-rich layer is directed from ester-rich layer evaporator 112 to fatty acid alkyl ester evaporator 122 for separation of at least a portion of the fatty acid alkyl esters from the ester-rich layer. It is to be understood, however, that the ester-rich layer can be directed from esterification vessel 30, following alcoholic esterification, to fatty acid alkyl ester evaporator 122 for recovery of fatty acid alkyl esters without solvolytic micellization of the ester-rich layer.

The fatty acid alkyl esters in the ester-rich layer are individually separated from the ester-rich layer in fatty acid alkyl ester evaporator 122 under conditions sufficient to prevent destroying the tocotrienols, thereby forming a tocotrienol-rich layer. An example of a suitable fatty acid alkyl ester evaporator 122 is a vacuum distillation apparatus constructed of glass.

Conditions sufficient to individually separate the fatty acid alkyl esters from the ester-rich layer without destroying the tocotrienols contained in the ester-rich layer include exposing the ester-rich layer in fatty acid alkyl ester evaporator 122 to a temperature in the range of between about 120° C. and about 200° C. at an absolute pressure in the range of between about one mm Hg and about ten mm Hg for a period of time sufficient to volatilize and thereby substantially remove fatty acid alkyl esters contained in the ester-rich layer. In a preferred embodiment, the absolute pressure during separation of the fatty acid alkyl esters from the ester-rich layer is about five mm Hg.

Substantially all fatty acid alkyl esters are individually separated and removed from the ester-rich layer by evaporating the fatty acid alkyl esters in order of decreasing volatility. Volatilization of fatty acid alkyl esters from the ester-rich layer causes remaining material in fatty acid alkyl ester evaporator 122 which is not volatilized, to form a tocotrienol-rich layer. The tocotrienol-rich layer contains a substantial portion of tocotrienols and lesser portions of carotenoids and fatty acid alkyl esters contained in the ester-rich layer.

The volatilized fatty acid alkyl esters are condensed in fatty acid alkyl ester condenser 124 and collected separately in receptacle 126. Examples of individual fatty acid alkyl esters which can be volatilized and removed from the ester-rich layer include alkyl palmitate, alkyl oleate, alkyl linoleate and alkyl stearate.

Individual tocotrienols are then adsorptively separated from the tocotrienol-rich layer under conditions sufficient to individually separate the tocotrienols from the tocotrienol-rich layer. Individual tocotrienols include γ-tocotrienol, δ-tocotrienol, α-tocotrienol, etc. In one embodiment, the tocotrienol-rich layer formed in fatty acid alkyl ester evaporator 122 is directed from fatty acid alkyl ester evaporator 122 to tocotrienol-rich layer recovery vessel 128. It is also to be understood that the ester-rich layer can be directed from ester-rich layer evaporator 112 to tocotrienol layer recovery vessel 128 for separation of fatty acid alkyl esters and individual separation of tocotrienols contained within the ester-rich layer.

Tocotrienol recovery vessel 128 is suitable for individually separating tocotrienols in the tocotrienol-rich layer. In one embodiment, the tocotrienol recovery vessel 128 has a length of between about ten centimeters and about fifty centimeters and an internal diameter of between about one centimeter and about five centimeters. Tocotrienol recovery vessel 128 is wet-packed with a suitable adsorbent 130 for separating tocotrienols from the tocotrienol-rich layer. Examples of suitable adsorbents include alumina, silica gel, silicic acid, magnesium oxide, calcium hydroxide, magnesium hydroxide, powdered sugar and cellulose. In a preferred embodiment, the adsorbent is alumina, 100/200 mesh grade packing. The adsorbent is wet-packed with a suitable solvent. An example of a suitable solvent in which the adsorbent is wet-packed is hexane.

The amount of adsorbent 130 in tocotrienol recovery vessel 128 is sufficient to substantially adsorb the tocotrienol-rich layer directed into tocotrienol recovery vessel 128. In one embodiment, the amount of adsorbent 130 is in the range of between about 0.2 gram and about five grams per gram of tocotrienol-rich layer directed to tocotrienol recovery vessel 128. In a preferred embodiment, about 0.5 gram of adsorbent per gram of tocotrienol-rich layer is contained in tocotrienol recovery vessel 128.

The tocotrienol-rich layer in tocotrienol recovery vessel 128 contacts adsorbent 130 contained in tocotrienol-rich layer recovery vessel 128. In a preferred embodiment, the tocotrienol-rich layer is contacted with adsorbent 130 by gravity feed of the tocotrienol-rich layer into the top of tocotrienol recovery vessel 128.

Fatty acid alkyl esters and carotenoids in the tocotrienol-rich layer are eluted from adsorbent 130 in tocotrienol recovery vessel 128 by contacting adsorbent 130 with a suitable eluant. Examples of suitable eluants include medium-length chain alkyl hydrocarbons. Examples of suitable medium-length chain alkyl hydrocarbons include hexane, heptane, petroleum ether, etc. In one embodiment, the fatty acid alkyl esters are eluted by directing a suitable solvent, such as hexane, from hexane source 98 through tocotrienol recovery vessel 128 to substantially elute fatty acid alkyl esters from adsorbent 130. The eluant containing the fatty acid alkyl esters is collected in receptacle 132 as an eluate fraction. The total volume of hexane used to elute the fatty acid alkyl esters and carotenoids can be in the range of between about 0.3 ml and about five milliliters per gram of tocotrienol-rich layer in tocotrienol-rich recovery vessel 128. In a preferred embodiment, about one milliliter of hexane per gram of tocotrienol-rich layer is employed.

Tocotrienols adsorbed by adsorbent 130 are then eluted from the tocotrienol recovery vessel 128 to form eluate fractions containing separated tocotrienols. An eluant is directed by gravity feed through tocotrienol recovery vessel 128, whereby the eluant contacts adsorbent 130 and the adsorbed tocotrienol-rich layer.

In one embodiment, the tocotrienols in the tocotrienol-rich layer can be concentrated by elution with a relatively pure lower alkyl alcohol. The eluant employed to elute the tocotrienols is a lower alkyl alcohol. In a preferred embodiment, the eluant is isopropanol. The isopropanol is directed from isopropanol source 100 to tocotrienol recovery vessel 128 in an amount sufficient to individually separate adsorbed tocotrienols in the tocotrienol-rich layer. In one embodiment, the total volume of eluant employed to separate and elute the tocotrienols is in the range of between about 0.1 ml and about five milliliters per gram of the tocotrienol-rich layer absorbed by adsorbent 130 in tocotrienol recovery vessel 128. In a preferred embodiment, the volume of the eluant is about 1.5 ml per gram of the adsorbed tocotrienol-rich layer.

In another preferred embodiment, tocotrienols in the tocotrienol-rich layer can be concentrated and individually separated during elution from tocotrienol recovery vessel 92. The individual tocotrienols can be concentrated and separated by elution with an eluant which comprises an eluant admixture of a suitable medium-length chain hydrocarbon and a lower alkyl alcohol. In a particularly preferred embodiment, the eluant admixture contains isopropanol in the range of between about one percent and about fifteen percent by volume and contains hexane in the range of between about eighty-five percent and about ninety-nine percent by volume. The eluant admixture is prepared by suitably combining, such as by agitation, hexane from hexane source 98 and isopropanol from isopropanol source 100 and eluant admixing vessel 102.

The eluant admixture is directed from eluant admixing vessel 102 to tocotrienol recovery vessel 128 in an amount sufficient to substantially separate and elute individual tocotrienols from the adsorbed tocotrienol-rich layer. In one embodiment, the total volume of eluant admixture employed to separate and elute the tocotrienols is in the range of between about two volumes and about twenty volumes per volume of the adsorbed tocotrienol-rich layer unconcentrated by vacuum evaporation. In a preferred embodiment, the volume of eluant admixture is about ten times that of the tocotrienol-rich layer.

The relative amounts of the hexane and the isopropanol is increased as tocotrienols are eluted from tocotrienol recovery vessel 128 so that the eluant admixture changes in concentration of isopropanol as elution of the individual tocotrienols proceeds. The concentration of isopropanol is increased either continuously or incrementally. In a preferred embodiment, the increase in concentration of lower alkyl alcohols is obtained in two percent increments from about one percent to about fifteen percent by volume of eluant admixture during elution of individual tocotrienols from tocotrienol recovery vessel 128.

Tocotrienols are separated and eluted from tocotrienol recovery vessel 128 in eluate fractions. Each eluate fraction is collected in a separate and empty receptacle 132. One eluate fraction of tocotrienols eluted from tocotrienol recovery vessel 128 contains a greater concentration of γ-tocotrienol than δ-tocotrienol or α-tocotrienol. A subsequent eluate fraction of tocotrienols eluted contains a greater portion of δ-tocotrienol than γ-tocotrienol or α-tocotrienol. It is to be understood that the order of elution of α-, γ- and δ-tocotrienols can vary according to the eluant as well as the adsorbent used.

Eluant can be removed from the eluate fractions containing the separated tocotrienols under conditions which prevent destroying the tocotrienols. In one embodiment, each eluate fraction is directed from receptacle 132 to vacuum evaporator 134. An example of a suitable vacuum evaporator 134 is a Buchi 461 model rotavaporizer. The eluant in each eluate fraction is then evaporated under suitable condition In a preferred embodiment, the eluant is evaporated at a temperature in the range of between about 25° C. and about 45° C. and at an absolute pressure in the range of between about ten mm Hg and about forty mm Hg during evaporation and removal of the eluant. The rotavaporized eluate fractions contain substantially separated individual tocotrienols.

Following elution of fatty acid alkyl esters, carotenoids and tocotrienols from the tocotrienol-rich layer, adsorbent 130 contained in tocotrienol recovery vessel 128 can be regenerated for reuse. It is to be understood, however, that regeneration of adsorbent 130 is not required after each elution. In one embodiment, adsorbent 130 is regenerated by contact with a suitable eluant in an amount sufficient to substantially remove remaining components of the tocotrienol-rich layer from adsorbent 130. An example of a suitable eluant includes methanol. In one embodiment, the amount of eluant employed is in the range of between about 0.5 volume and about five volumes per volume of tocotrienol-rich layer introduced to tocotrienol recovery vessel 128.

The glycerol-rich layer formed by alcoholic esterification of the crude palm oil is esterification vessel 30 and the water layer employed to wash residual sodium hydroxide from the ester-rich layer are suitably combined, such as by agitation, in neutralization vessel 40. The glycerol-rich layer containing the water layer is then neutralized under conditions suitable to prevent substantial degradation of the glycerol in the glycerol-rich layer. In one embodiment, a suitable acid is directed from acid source 136 to neutralization vessel 40 in an amount sufficient to substantially neutralize the glycerol-rich layer. An example of a suitable acid is hydrochloric acid (HCl). In a particularly preferred embodiment, the hydrochloric acid directed to neutralization vessel 40 is in the form of a solution having a concentration of about six molar. The glycerol-rich layer is agitated by a suitable means, such as by an agitator, not shown, during addition of acid. The temperature of the glycerol-rich layer during neutralization is maintained in a range of between about 20° C. and about 35° C. The pH of the glycerol layer is lowered by addition of acid to a range of between about six and about eight.

Following neutralization, the glycerol-rich layer is settled at a temperature in the range of between about 10° C. and about 40° C., thereby allowing a layer of wax to form at the top of the glycerol-rich layer. The wax layer is then removed from the glycerol-rich layer by a suitable method. An example of a suitable method of removing the wax layer from the glycerol-rich layer is centrifugation. Wax collected from glycerol-rich layer in neutralization vessel 40 is directed to wax collection vessel 138.

The glycerol-rich layer from which the wax layer has been removed can they be exposed to conditions sufficient to substantially remove water from the glycerol-rich layer. In one embodiment, the glycerol-rich layer is directed from neutralization vessel 40 to glycerol-rich layer evaporator 140. The glycerol-rich layer is heated in glycerol-rich layer evaporator 140 to a temperature in the range of between about 65° C. and about 140° C. at atmospheric pressure for a period of time sufficient to substantially evaporate the water from the glycerol-rich layer. The undistilled material comprises glycerol and the sodium chloride salt.

The glycerol and sodium chloride are cooled to a temperature in the range of between about 20° C. and about 30° C. Glycerol is separated from the sodium chloride by directing the glycerol from glycerol-rich layer evaporator 140 into glycerol holding vessel 142. Residual sodium chloride contained in the glycerol in glycerol holding vessel 142 is removed by dissolving the glycerol with a suitable solvent, wherein the sodium chloride remains substantially undissolved. An example of a solvent is isopropanol. In one embodiment, the glycerol is dissolved by directing isopropanol from solvent source 144 to glycerol holding vessel 142 and is combined with the glycerol contained therein. The amount of isopropanol combined with the glycerol can be between about one volume and about ten volumes per volume of glycerol. In a particularly preferred embodiment, the glycerol is combined with about five volumes of solvent per volume of glycerol. The combined glycerol and solvent are then agitated by a suitable means, such as by an agitator, not shown, for a period of time in the range of between about one minute and about ten minutes at a temperature in the range of about 20° C. and about 30° C. The sodium chloride remains undissolved during the period of agitation.

Undissolved sodium chloride is then removed from the glycerol and solvent by filtration. In one embodiment, dissolved glycerol and undissolved sodium chloride are directed from glycerol holding vessel 142 through filter 146. The glycerol and solvent thereby form a filtrate which is collected from filter 146 in glycerol filtrate collection vessel 148.

The filtrate contained in filtrate collection vessel 148 is then exposed to conditions sufficient to remove the solvent, such as by vacuum evaporation. In one embodiment, the filtrate is directed from glycerol filtrate collection vessel 148 to filtrate evaporator 150. The filtrate is exposed in filtrate evaporator 150 to a temperature in the range of between about 35° C. and about 50° C. at an absolute pressure in the range of between about ten mm Hg and about thirty-five mm Hg for a period of time sufficient to substantially evaporate and remove the solvent from the glycerol. The remaining glycerol in filtrate evaporator 150 is then directed from filtrate evaporator 150 to distillation column 152. The glycerol is distilled in distillation column 152. In a preferred embodiment, the glycerol is distilled at a temperature of about 200° C. at an absolute pressure of about five millimeters Hg under suitable conditions to thereby purify the glycerol.

The invention will now be further and specifically described by the following examples. All parts and percentages are by weight unless otherwise stated.

EXAMPLE I

Solvolytic micellization of fatty acid methyl esters and carotenoids, derived by esterification with a two percent solution of sodium hydroxide in methanol and crude palm oil, was performed by first dissolving about 1000 ml of an ester-rich layer, including carotenoids to be concentrated, in about 5000 ml of methanol at room temperature. The solution was agitated and about 250 ml of water was added. An upper ester-rich layer, having a volume of about 700 ml was decanted. A lower carotenoid-rich layer having a volume of about 300 ml had a concentration of carotenoids of about 1500 ppm. A solvolytic micellization was conducted wherein the lower carotenoid-rich layer was combined with about 1500 ml of methanol, followed by addition of about 75 ml of water to form a lower carotenoid-rich layer having a volume of about 100 ml. This second lower carotenoid-rich layer had a concentration of carotenoids of about 4500 ppm. About 500 ml of methanol was added to the lower carotenoid-rich layer followed by addition of about 25 ml of water for a third solvolytic micellization. A lower layer formed having a volume of about 24 ml and a carotenoid concentration of about 25,000 ppm. In a fourth solvolytic micellization, about 100 ml of methanol was added to the lower carotenoid-rich layer and then about five ml of water was added. A lower carotenoid-rich layer was thereby formed having a volume of about four ml. The lower carotenoid-rich layer was rotavaporized in a Buchi 451 rotavaporizer at a temperature of 45° C. and an absolute pressure of about 25 mm Hg for a sufficient time to remove residual methanol.

The concentration of the carotenoids in the carotenoid rich layer was determined by spectrophotometry using a Hewlett Packard 8425A diode array spectrophotometer. The carotenoid-rich paste was then dissolved in hexane sufficient to obtain a reading from the spectrophotometer of less than 1,000 milli-absorbence units. The spectrophotometer was set at a wavelength of 444 nanometers. The concentration of the carotenoid-rich layer was measured by comparing the concentration of the diluted sample of carotenoid-rich layer to a sample having a known concentration of carotenoids. The concentration of the lower carotenoid-rich layer following rotavaporization as determined by spectrophotometry was about 100,000 ppm (or about 100 mg/ml). Yield of carotenoid recovery from the esterified solution of fatty acid methyl esters and carotenoids ranged from about 70% to about 90%.

EXAMPLE II

A ten ml sample containing about 2.4% of carotenoids and about 97.6% of fatty acid methyl esters was combined with about forty ml of a solution of potassium hydroxide and methanol to form a reaction mixture. The concentration of potassium hydroxide in hydroxide in the methanol was about seventeen percent weight per volume of methanol. The reaction mixture was agitated at about room temperature for a period of time of about three hours to saponify the fatty acid methyl esters. Following agitation, the carotenoids were extracted from the reaction mixture with petroleum ether. Twenty-five ml of petroleum ether was added to the reaction mixture. The petroleum ether and the reaction mixture were then agitated for less than two minutes at a temperature of 25° C. The petroleum ether and the reaction mixture were then settled for five minutes, during which time a lower reaction mixture layer and an upper solvent layer formed. The lower reaction mixture layer and the upper solvent layer were separated and a second extraction was conducted using the reaction mixture layer and 25 ml of petroleum ether. A lower reaction mixture layer and an upper solvent layer which were formed by the second extraction were separated and a third extraction was conducted employing the lower reaction mixture layer formed during the second extraction and 25 ml of petroleum ether. A fourth extraction was conducted employing the lower reaction mixture layer formed during the third extraction and 25 ml of petroleum ether. The upper solvent layer formed during the extraction were combined and then washed with five successive portions of 1.5M aqueous sodium chloride solution.

A substantial portion of the solvent contained in the washed and combined solvent layers was removed by immersion of the bottom portion of a Buchi 451 rotavaporizer, containing the washed and combined solvent layers in a water bath which was maintained at a temperature of 30° C. Vacuum was maintained in the rotavaporizer at an absolute pressure of about twenty-five millimeters Hg to thereby evaporate the petroleum ether contained in the combined solvent layers. Vacuum evaporation was continued until a carotenoid-rich paste was formed in the rotavaporator. The carotenoid-rich paste was removed from the rotavaporator and placed in a flask. Residual petroleum ether was removed from the carotenoid-rich paste by directing nitrogen into the flask at a temperature of 25° C. for a period of time of five minutes to obtain a dried carotenoid-rich paste. The weight of the dried carotenoid-rich paste was 9.5 grams.

The concentration of carotenoids in the carotenoid-rich paste was determined by spectrophotometry using a Hewlett Packard 8452A diode array spectrophotometer. The carotenoid-rich paste was diluted in hexane sufficient to obtain a reading from the spectrophotometer of less than 1,000 milli-absorbence units. The spectrophotometer was set at a wavelength of 444 nanometers. Concentration of the carotenoid-rich paste was measured by comparing the concentration of the diluted sample of carotenoid-rich paste to a sample having a known concentration. The concentration of the carotenoids in the carotenoid-rich paste, as determined by spectrophotometry, was 18.6%.

EXAMPLE III

An open column having a length of about twenty centimeters and an internal diameter of about one centimeter was wet-packed with hexane and alumina AG 7 100–200 mesh grade packing (0% water), commercially available from Bio-Rad, Inc. A carotenoid-rich layer was obtained by employing preferred conditions for miscellar fractionation and alcoholic esterification using methanol. The ester-rich layer formed was then exposed to three solvolytic micellizations with methanol. The carotenoid-rich layer formed by the three solvolytic micellizations was rotavaporized to remove residual methanol. A 0.5 gm sample of the rotavaporized carotenoid-rich layer having a concentration of carotenoids of about 5600 ppm (0.56 mg/ml) was added to the top of the column. An eluant, hexane, was then added to the column by gravity at a flow rate of about 1.25 ml/min. Fifty milliliter eluate fractions were collected from the bottom of the column. The first five eluate fractions were light yellow and contained fatty acid methyl esters eluted from the column. No carotenoids were detected in the first five eluate fractions. Diminished amounts of fatty acid methyl esters were detected in sixth and seventh eluate fractions. An eighth eluate fraction yielded no residue, indicating that no fatty acid methyl esters were present. After the eighth eluate fraction was collected, a solution of about ten percent isopropanol in hexane was directed through the column. All carotenoids were subsequently eluted and collected as a ninth eluate fraction which was dark yellow. The ninth eluate fraction was rotavaporized to substantially remove the eluant from the ninth eluate fraction and thereby form a rotavaporized sample. The concentration of the rotavaporized sample was then measured by spectrophotometer, such as was done in Examples I and II. The carotenoid concentration as measured by spectrophotometry was of about 180,000 ppm (180 mg/ml).

EXAMPLE IV

An open column having a length of about ten centimeters and an internal diameter of about 2.5 centimeters was wet-packed with hexane and alumina AG 7 100-200 mesh grade packing. 0.5 gm sample of fatty acid methyl esters having a concentration of carotenoids of about 5,000 ppm (0.5 mg/ml) was added to the packing at the top of the column. Four hundred milliliters of relatively pure hexane was directed through the column to elute the fatty acid methyl esters.

Three successive 50 ml volumes of eluant admixture containing hexane and incrementally increasing concentrations of isopropanol were then directed through the column to separate $\alpha$-carotene and $\beta$-carotene. The first 50 ml volume of eluant admixture had a hexane concentration of 99% and a isopropanol concentration of 1% by volume. The second 50 ml eluant admixture had concentrations of hexane and isopropanol of 98% and 2% by volume, respectively. The third 50 ml eluant admixture had concentrations of hexane and isopropanol of 95% and 5% by volume, respectively. The $\alpha$- and $\beta$-carotenes appeared in the column during direction of the three 50 ml eluant admixture volume through the column as two lower orange-red bands. A pink band appeared above the orange-red bands and a yellow band appeared above the pink band.

The orange-red bands and the pink and yellow bands were separated by removing the packing from the column. The bands were separately dissolved in a mixture comprising equal volumes of hexane and methanol and then filtered to remove the alumina packing. The resulting filtrates were rotavaporized and then dissolved in relatively pure hexane for identification by high pressure liquid chromatography (HPLC).

Analysis of HPLC was conducted on a Zorvax ODS column, having dimensions of about 25 cm $\times$ 0.46 cm. The mobile phase in the column was 60% acetonitrile, 36% methanol and 4% methylene chloride by volume. The flow rate through the column was two milliliters per minute at an absolute pressure of 135 bars. A diode array detector was used to determine the concentration of the carotenoids. The wavelength range of the diode array detector was set at 250-550 nanometers and the monitoring wavelength was set at 450 nanometers. Results of the HPLC analysis indicated that the yellow band contained xanthophylls and the pink band contained moderately polar carotenoids. About 95% of the carotenoids present in the lowest orange-red band were $\beta$-carotenes and the remaining 5% were $\alpha$-carotenes. About 5% of the carotenoids present in the orange-red band which was disposed between the lowest orange-red band and the pink band were $\beta$-carotenes and the remaining 95% were $\alpha$-carotenes.

EXAMPLE V

An open column having a length of about thirty centimeters and an internal diameter of about three centimeters was wet-packed with hexane and the same mesh grade of alumina as was used in Examples III and IV. About 2.65 gm of a rotavaporized sample obtained in the same manner as was the sample in Example III, but including an additional solvolytic micellization. The rotavaporized sample contained about 55,000 ppm of carotenoids and was introduced to the packing at the top of the column. Fatty acid methyl esters, as indicated by a light yellow band, were then eluted in eight 50 ml eluate fractions from the column using the same eluate as was used in Example III. The ninth eluate fraction eluted a dark yellow band containing carotenoids in a solution of isopropanol and hexane. The ninth eluate fraction was rotavaporized to form a rotavaporized sample as was the ninth eluate fraction in Example III, and then analyzed by a spectrophotometer as was done in Examples I-III. The carotenoid concentration of the rotavaporized sample was about 120,000 ppm (120 mg/ml).

EXAMPLE VI

An open column having a length of about ten centimeters and an internal diameter of about four centimeters was wet-packed with hexane and the same mesh grade of alumina as in Examples III-V. A rotavaporized sample of ester-rich layer having a weight of about five grams and containing fatty acid methyl esters, carotenoids and tocotrienols, obtained by alcoholic esterification of crude palm oil under the preferred conditions, but without solvolytic micellization, was added to the adsorbent at the top of the column. Eluant was added to the adsorbent at the top of the column in fifty milliliter aliquots. Table I, shown below, lists the relative proportion of hexane and isopropanol in each aliquot. The color of each eluate fraction collected following addition of solvent to the top of the column are also shown in Table I. The samples were rotavaporized, weighed, and then analyzed by HPLC on a Zorbax ODS column, having dimensions of about 25 cm $\times$ 0.46 cm. The mobile phase in the column was 95% acetonitrile and 5% methanol by volume. The flow rate through the column was about two milliliters per minute at an absolute pressure of about 135 bars. A fluorescence detector was used to determined the concentration of $\alpha$-, $\gamma$- and $\delta$-tocotrienols in the rotavaporized samples. The results of analysis by the fluorescence detector are listed in Table I. Detection settings for samples K and L were set at $\lambda_{ex}=290$ nm; $\lambda_{em}=330$ nm; and PMT=15. The sample interval through the detector was about 1,000 milliseconds. As can be seen in Table I, for example, tocotrienols were eluted by directing hexane and isopropanol through the column by gravity in the amount of about 3% by volume or greater. Also, γ-tocotrienol was recovered from the column before δ-tocotrienol or α-tocotrienol. Further, δ-tocotrienol was present in an amount greater than that of γ-tocotrienol when the solvent passing through the column was isopropanol alone. As can also be seen in Table I, the concentration of δ-tocotrienol in sample L and γ-tocotrienol in samples K and L were higher than that of crude palm oil.

EXAMPLE VIII

An open column having a length of about ten centimeters in length and an internal diameter of about four centimeters was wet-packed with alumina and hexane as in the Examples III–VII. A 250 ml sample of ester-rich layer containing fatty acid methyl esters, carotenoids and tocotrienols, obtained in the same manner as for Examples VI and VII, was directed onto the adsorbent at the top of the column. An eluant, hexane, was then directed through the column in an amount sufficient to separate and elute fatty acid methyl esters and carotenoids. Isopropanol was then directed through the column in an amount sufficient to collect an eluate fraction containing tocotrienols. The eluate fraction containing tocotrienols was rotavaporized as were the eluate fractions of Examples III–VII. The rotavaporized eluate fractions had a δ-tocotrienol concentration of about 93,000 ppm and a γ-tocotrienol concentration of about 31,900 ppm as measured by HPLC using a fluorescence detector as described in Examples VI and VII. Only a slight amount of α-tocotrienols were detected.

TABLE I

| Sample | Eluate Fraction | n-Hexane: Isopropanol | Color | Weight(g) | Concentration (ppm) of Tocotrienols δ- | γ- | α- |
| --- | --- | --- | --- | --- | --- | --- | --- |
| Control | Crude Palm Oil | — | — | — | 302 | 455 | 292 |
| A | 1 | 100:00 | Colorless | 0.117 | — | 39 | — |
| B | 2 | 100:00 | Dk yellow-orange | 2.190 | — | — | — |
| C | 3 | 100:00 | Lt yellow | 0.7475 | — | — | — |
| D | 4 | 99:1 | Colorless-yellow | 0.4935 | — | — | — |
| E | 5 | 99:1 | Colorless | 0.2550 | — | — | — |
| F | 6 | 98:2 | Colorless | 0.2100 | — | — | — |
| G | 7 | 98:2 | Colorless | 0.1936 | — | — | — |
| H | 8 | 97:3 | Colorless | 0.1300 | — | — | — |
| I | 9 | 97:3 | Dk yellow-orange | 0.3194 | — | 130 | — |
| J | 10 | 96:4 | Dk yellow-orange | 0.1450 | 353 | 204 | 24 |
| K | 11 | 96:4 | Lt yellow | 0.0214 | 54 | 1850 | 301 |
| L | 12–14 | 0:100 | Lt yellow | 0.1520 | 2876 | 1329 | 100 |

EXAMPLE VII

A column having a length of about ten centimeters and an internal diameter of about three centimeters was wet-packed with alumina and hexane as in Examples III–VI. A rotavaporized sample having a weight of about 4.2 gm containing fatty acid methyl esters, carotenoids and tocotrienols, which was obtained in the same manner as the ester-rich layer of Example VI, was introduced to the top of the column. An admixture of about 250 ml of hexane and isopropanol wherein the concentration of isopropanol was in an amount ranging from about two percent to about four percent was directed through the column until all fatty acid methyl esters, as indicated by a light yellow band, and carotenoids, as indicated by a first dark yellow band, were eluted from the column. Fifty milliliters of relatively pure isopropanol was then directed through the column, thereby separating and eluting α-tocotrienol, γ-tocotrienol, and then δ-tocotrienol which were indicated by a second and third dark yellow bands, respectively. The eluate containing the tocotrienols were collected to form two 25 ml eluate fractions. The eluate fractions collected were rotavaporized as were the eluate fractions obtained in Examples III–VI.

The concentration of tocotrienols was measured by HPLC using a fluorescence detector as described in Example VI. The rotavaporized first eluate fraction contained a γ-tocotrienol concentration of about 38,500 ppm and α-tocotrienol concentration of about 11,500 ppm. The rotavaporized second eluate fraction had a δ-tocotrienol concentration of about 10,200 ppm and a α-tocotrienol concentration of about 562 ppm.

EXAMPLE IX

Ester-rich layers containing fatty acid methyl esters and tocotrienols were recovered using a preferred embodiment of solvolytic micellization. The combined ester-rich layers were vacuum distilled to obtain a 200 ml sample of residue containing fatty acid methyl esters and tocotrienols. This residue was further vacuum distilled to remove fatty acid methyl esters and thereby obtain a 4.12 gm sample of residue comprising tocotrienols. The residue was introduced to an open column, having a length of about ten centimeters and an internal diameter of about three centimeters, and wet-packed with alumina and hexane as were the columns in Examples III–VIII. Thirty milliliters of n-hexane was then directed through the column to elute fatty acid methyl esters remaining in the residue. Tocotrienols were then separated and eluted from the column by directing fifty milliliters of isopropanol through the column. The eluate fraction collected from the column was rotavaporized to obtain an eluate residue of 0.204 gm. The concentration of α-, γ- and δ-tocotrienols in the eluate residue was determined by HPLC using a fluorescence detector as described in Examples IV–VII. The concentration of α-, γ- and δ-tocotrienols in the rotavaporized eluate fraction is listed in Table II, below:

TABLE II

| Vitamin E compound | Concentration (ppm) |
|---|---|
| δ-tocotrienol | 12,986 |
| γ-tocotrienol | 67,340 |
| α-tocotrienol | 126,728 |
| Total tocotrienols | 207,054 |

The concentration of tocotrienols in the rotavaporized eluate fraction is about 266 times that of crude palm oil.

EXAMPLE X

A ten milliliter sample of fatty acid methyl esters obtained from crude palm oil and containing 1.1% of tocotrienols and tocopherols was added to the top of an open column. The column had an inside diameter of ten millimeters and a length of fifty-seven millimeters. The column was wet-packed with five grams of alumina of the same type used in Examples III-IX. The alumina packing was wet-packed in hexane. After the sample had been adsorbed by the packing, the dead volume of the hexane was eluted from the column. The fatty acid methyl esters, which could be seen as a light yellow band, were eluted by directing 4.65 ml of hexane through the column as an eluant. The tocotrienols and tocopherols, which could be seen as a dark yellow band, were eluted by directing ten milliliters of methanol through the column as an eluant. A methanol eluate fraction was collected and rotavaporized under the same conditions as were the eluate fractions in Examples III-IX to form a 0.167 gm rotavaporized sample. The concentration of tocotrienols and tocopherols in the rotavaporized sample was measured by HPLC using a fluorescence detector as described in Examples VI-IX. The concentration of the tocotrienols and tocopherols in the rotavaporized sample was 56.4% by weight.

Equivalents

Those skilled in the art will recognize or be able to ascertain using no more than routine experimentation, many equivalents to the specific embodiments of the invention described specifically herein. Such equivalents are intended to be encompassed in the scope of the following claims.

We claim:

1. A process for extracting carotenoids and tocotrienols from oils, comprising:
   a) contacting the oil with a lower alkyl alcohol in the presence of a base under conditions sufficient to convert glycerides in the oil to fatty acid alkyl esters and glycerol and to form an ester-rich layer and a glycerol-rich layer;
   b) separating the ester-rich layer from the glycerol-rich layer;
   c) contacting the ester-rich layer with a lower alkyl alcohol and water under conditions sufficient to cause solvolytic micellization of the ester-rich layer without destroying the carotenoids and tocotrienols, thereby forming a carotenoid-rich layer;
   d) separating the ester-rich layer from the carotenoid-rich layer;
   e) separating the lower alkyl alcohol from the ester-rich layer under conditions sufficient to prevent destroying the tocotrienols in the ester-rich layer;
   f) separating the fatty acid alkyl esters from the ester-rich layer by exposing the ester-rich layer to a temperature and pressure sufficient to substantially volatilize and remove at least a portion of the fatty acid alkyl esters from the ester-rich layer and to prevent destroying the tocotrienols, thereby forming a tocotrienol-rich layer; and
   g) adsorptively separating and concentrating individual tocotrienols in the tocotrienol-rich layer.

2. A process of claim 1 further comprising the step of adsorptively separating individual carotenoids from the carotenoid-rich layer.

3. A process of claim 2 wherein adsorptively separating individual carotenoids from the carotenoid-rich layer includes contacting the carotenoid-rich layer with an adsorbent and then contacting the carotenoid-rich layer with an eluant admixture, whereby individual carotenoids are separated and eluted form the adsorbent.

4. A process of claim 1 further comprising the steps of contacting the carotenoid-rich layer with a base under conditions sufficient to substantially saponify the fatty acid alkyl esters contained in the carotenoid-rich layer and then contacting the carotenoid-rich layer and base with a medium-length chain hydrocarbon under conditions sufficient to extract a substantial portion of the carotenoids from the carotenoid-rich layer.

5. A process of claim 4 wherein contacting the oil with a lower alkyl alcohol and a base includes contacting the oil with an esterification solution comprising a lower alkyl alcohol and a base.

6. A process of claim 5 wherein the conditions sufficient to convert glycerides in the oil to fatty acid alkyl esters and glycerol and to form an ester-rich layer and a glycerol-rich layer include exposing the esterification solution and the ester-rich layer to a temperature in the range of between about 35° C. and about 70° C. over a period of time in the range of between about 0.5 hours and about four hours.

7. A process of claim 6 wherein the base comprises sodium hydroxide present in the esterification solution in the amount of between about 0.1% by weight and about three percent by weight of the esterification solution.

8. A process of claim 7 wherein the esterification solution contacted with the oil is present in an amount in the range of between about 0.2 grams and about one gram per gram of oil.

9. A process of claim 8 wherein the amount of lower alkyl alcohol contacted with the ester-rich layer during solvolytic micellization is in the range of between about three volumes and about ten volumes per volume of ester-rich layer.

10. A process of claim 9 wherein the amount of water contacted with the ester-rich layer is in the range of between about one percent and about six percent of the total volume of lower alkyl alcohol combined with the ester-rich layer.

11. A process of claim 10 wherein the lower alkyl alcohol is separated from the ester-rich layer by exposing the ester-rich layer to a temperature in the range of between about 35° C. and about 50° C. and at an absolute pressure in the range of between about twenty millimeters Hg and about one hundred millimeters Hg over a period of time sufficient to substantially volatilize and remove the lower alkyl alcohol from the ester-rich layer.

12. A process of claim 11 wherein the fatty acid alkyl ester is separated from the ester-rich layer by exposing the ester-rich layer, from which the lower alkyl alcohol has been substantially removed, to a temperature in the range of between about 120° C. and about 200° C. and at an absolute pressure in the range of between about one mm Hg and about ten mm Hg, over a period of time sufficient to substantially volatilize and remove fatty acid alkyl esters from the ester-rich layer, thereby forming a tocotrienol-rich layer.

13. A process of claim 12 wherein adsorptively separating individual tocotrienols from the tocotrienol-rich layer includes contacting the tocotrienol-rich layer with an adsorbent and then contacting the tocotrienol-rich layer with an eluant, whereby tocotrienols are eluted from the adsorbent.

14. A process of claim 13 wherein eluant comprises an eluant admixture.

15. A process of claim 14 further comprising the step of contacting the crude palm oil with a solvent under conditions sufficient to cause at least a portion of glycerides containing saturated fatty acids to precipitate from the crude palm oil, whereby a solvent layer is formed containing the precipitated glycerides.

16. A process of claim 15 further comprising the step of separating the solvent layer containing the precipitated saturated fatty acids from the crude palm oil.

17. A process of claim 16 wherein the solvent layer containing the precipitated glycerides is formed by exposing the crude palm oil and the solvent to a temperature in the range of between about −20° C. and about 5° C. for a period of time in the range of between about five hours and about twenty hours.

18. A process of claim 17 further comprising the step of separating the precipitated glycerides from the solvent layer.

19. A process of claim 18 wherein the precipitated glycerides are separated from the solvent layer by filtration.

20. A process of claim 19 further comprising the steps of:
 a) contacting the glycerol-rich layer with a sufficient amount of acid to lower the pH of the glycerol-rich layer to a range of between about six and about eight;
 b) exposing the glycerol-rich layer to conditions sufficient to substantially remove the water from the glycerol-rich layer and to form a glycerol precipitate and a salt precipitate;
 c) contacting the glycerol-rich layer with a solvent in an amount sufficient to substantially dissolve the precipitated glycerol while the salt substantially remains as a salt precipitate;
 d) separating the salt precipitate from the glycerol-rich layer; and
 e) exposing the glycerol-rich layer and the solvent to conditions sufficient to remove the solvent from the glycerol-rich layer.

21. A process of claim 20 wherein the adsorbent is selected from the group comprising alumina, silica gel, salicic acid, magnesium oxide, magnesium hydroxide, calcium oxide, powdered sugar and celluose.

22. A process for extracting carotenoids and tocotrienols from oils, comprising:
 a) contacting the oil with a lower alkyl alcohol in the presence of a base under conditions sufficient to convert glycerides in the oil to fatty acid alkyl esters and glycerol and to form an ester-rich layer and a glycerol-rich layer;
 b) separating the ester-rich layer from the glycerol-rich layer;
 c) contacting the ester-rich layer with a lower alkyl alcohol and water under conditions sufficient to cause solvolytic micellization of the ester-rich layer without destroying the carotenoids and tocotrienols, thereby forming a carotenoid-rich layer;
 d) separating the ester-rich layer from the carotenoid-rich layer;
 e) separating the lower alkyl alcohol from the ester-rich layer under conditions sufficient to prevent destroying the tocotrienols in the ester-rich layer;
 f) separating the fatty acid alkyl esters from the ester-rich layer by exposing the ester-rich layer to a temperature and pressure sufficient to substantially volatilize and remove at least a portion of the fatty acid alkyl esters from the ester-rich layer and to prevent destroying the tocotrienols, thereby forming a tocotrienol-rich layer; and
 g) adsorptively separating and concentrating individual tocotrienols in the tocotrienol-rich layer.

* * * * *